United States Patent [19]
Barrack, Jr. et al.

[11] Patent Number: 5,899,869
[45] Date of Patent: May 4, 1999

[54] ORTHOPEDIC APPLIANCE WITH WEIGHT ACTIVATED BRAKE AND VARIABLE EXTENSION ASSIST

[76] Inventors: Herb J. Barrack, Jr., 5161 Avenida Playa Cancun, San Diego, Calif. 92124; Ronald Hallam, 1102 Alpine Oaks Dr., Alpine, Calif. 91901; Albert Williams, 1737 Navaja Rd., El Cajon, Calif. 92020

[21] Appl. No.: 08/996,088

[22] Filed: Dec. 22, 1997

[51] Int. Cl.⁶ ..................................... A61F 5/00
[52] U.S. Cl. ................................ 602/16; 623/43
[58] Field of Search ......................... 602/16, 26; 623/43, 623/44

[56] References Cited

U.S. PATENT DOCUMENTS

| | | | |
|---|---|---|---|
| 2,522,853 | 9/1950 | Black | 602/16 |
| 2,558,986 | 7/1951 | Seelert | 602/16 |
| 2,559,473 | 7/1951 | Slodek, Sr. | 602/16 |
| 3,309,715 | 3/1967 | Nader et al. | |
| 3,673,613 | 7/1972 | Asbelle et al. | |
| 3,826,251 | 7/1974 | Ross | 602/16 |
| 4,005,496 | 2/1977 | Wilkes | |
| 4,051,558 | 10/1977 | Vallotton | |
| 4,135,254 | 1/1979 | Weber et al. | |
| 4,252,111 | 2/1981 | Chao et al. | 602/16 |
| 4,502,472 | 3/1985 | Pansiera | 602/16 |
| 4,595,179 | 6/1986 | Glabiszewski | |
| 4,617,920 | 10/1986 | Carsalade | |
| 4,685,926 | 8/1987 | Haupt | |
| 4,685,927 | 8/1987 | Haupt | |
| 5,044,360 | 9/1991 | Janke | 602/16 |
| 5,092,902 | 3/1992 | Adams et al. | |
| 5,171,325 | 12/1992 | Aulie | |
| 5,376,134 | 12/1994 | Biedermann | 602/16 |
| 5,490,831 | 2/1996 | Myers et al. | 602/16 |

OTHER PUBLICATIONS

Popular Science, May '97, p. 27 Dual Position Brace.

*Primary Examiner*—Linda C.M. Dvorak
*Attorney, Agent, or Firm*—Gene Scott-Patent Law & Venture Group

[57] ABSTRACT

A weight bearing strut assembly is capable of supporting the human frame in the act of walking and further enables a leg to which it is strapped to bend in a normal manner as the leg is brought forward during each step, and to lock when the leg is straightened as necessary to shift weight thereupon. The strut assembly includes a braking mechanism activated as load is placed upon the strut assembly, and an urging mechanism which is activated when the load is removed, and the strut assembly is bent but moving toward the straight leg attitude. Under these conditions, the urging mechanism drives the strut assembly quickly into a co-linear arrangement so as to assure that the strut assembly is ready to take a compressive load.

7 Claims, 4 Drawing Sheets

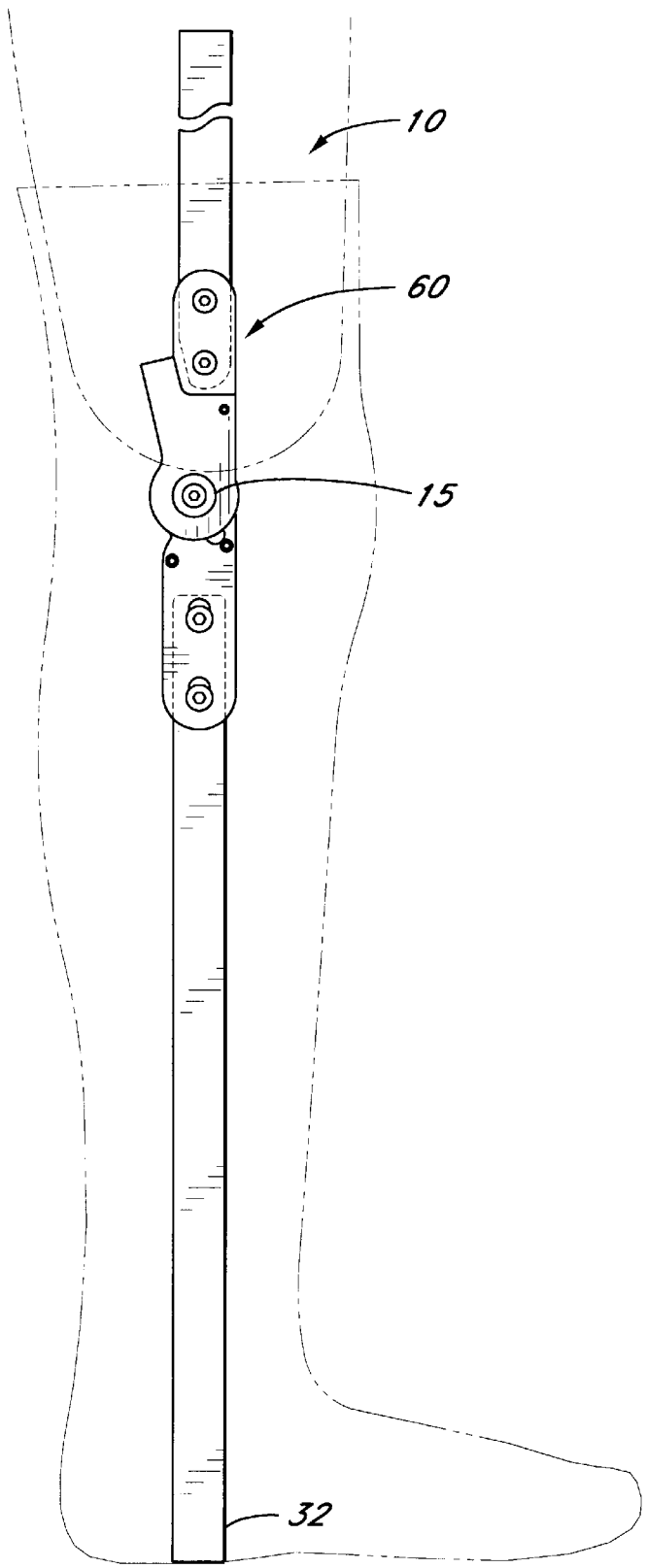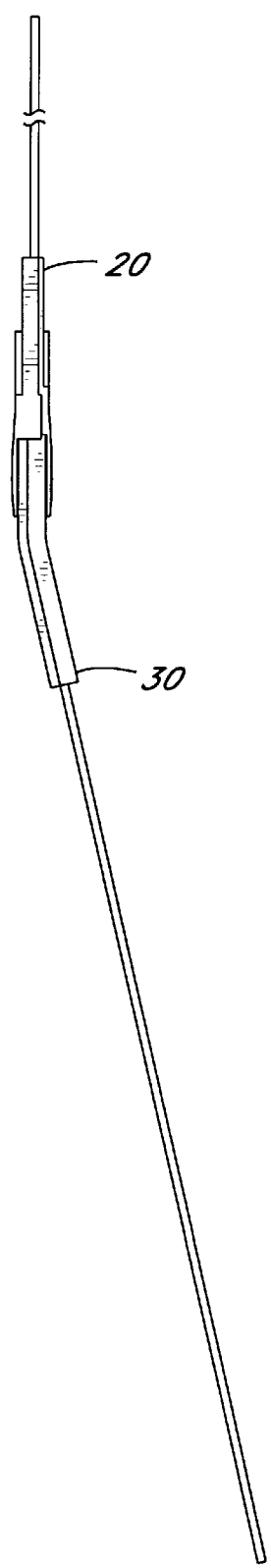

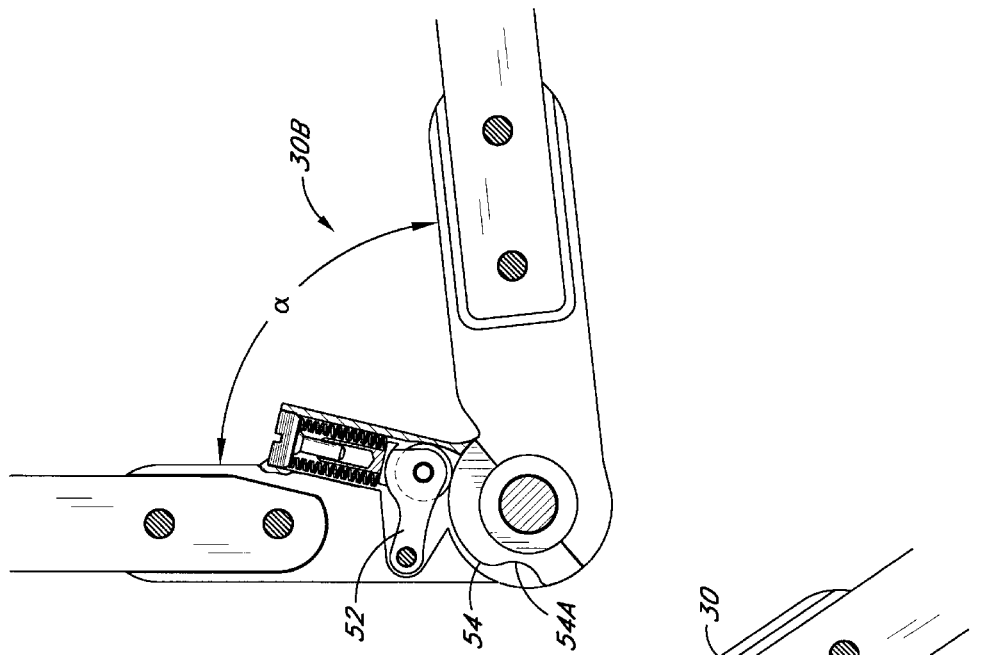
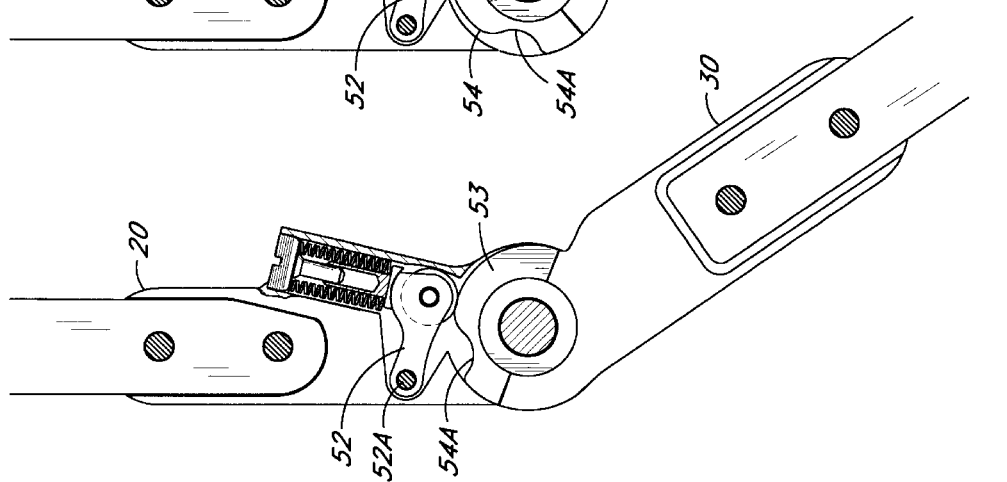
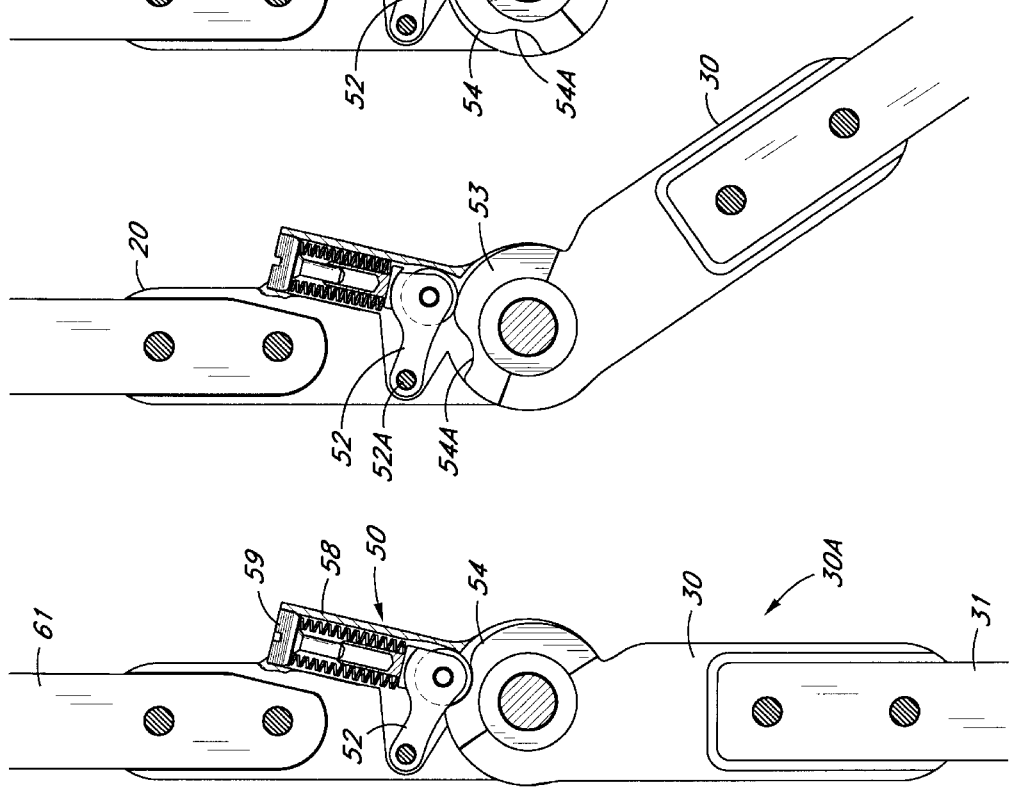

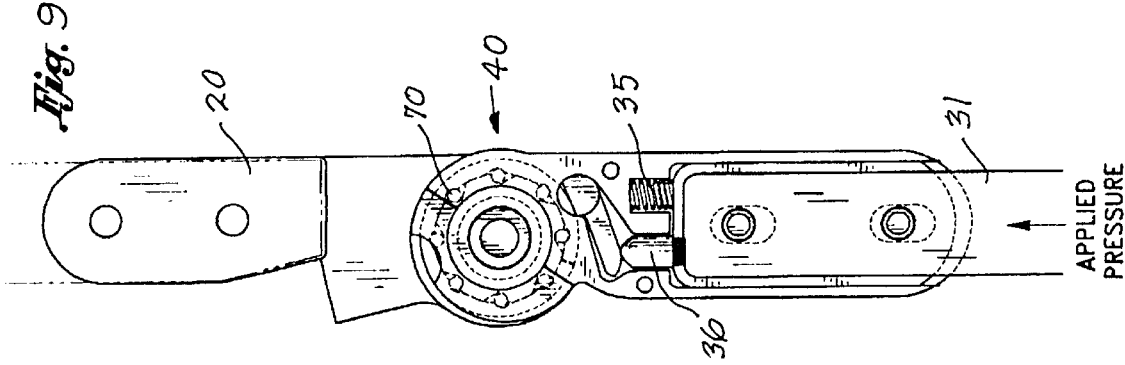
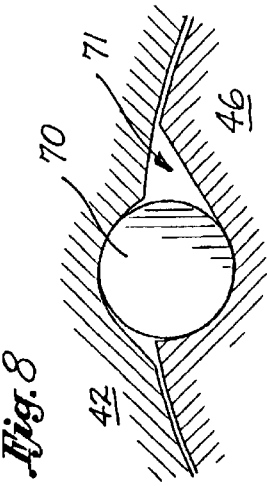
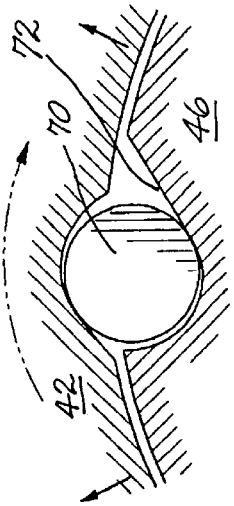
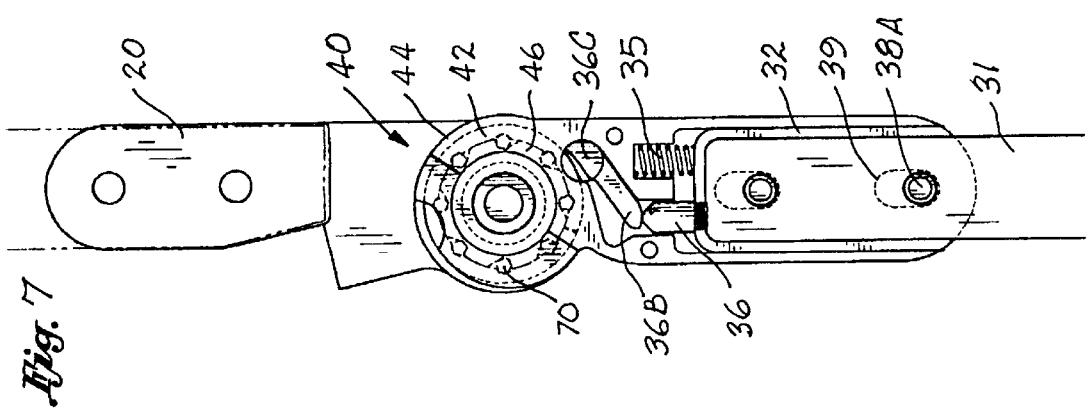

ORTHOPEDIC APPLIANCE WITH WEIGHT ACTIVATED BRAKE AND VARIABLE EXTENSION ASSIST

BACKGROUND OF THE INVENTION

1. Field of the Invention

This invention relates generally to orthopaedic appliances, and more particularly to one such appliance for support in the act of human limb manipulation such as in walking wherein the appliance enables improved motor motion.

2. Description of Related Art

The following art defines the present state of this field:

Carsalade, U.S. Pat. No. 4,617,920 describes a device for facilitating practice of downhill skiing which includes for each lower limb a knee bandage having two suitable curved and profiled plates, one of which wraps up the thigh while the other wraps down the leg, being adapted to cooperate with a part of the user's shoe; the upper plate is continued downward by two opposite and parallel arms profiled and articulated each on a shaft, on either side of the knee, the lower plate being continued upward by two opposite and parallel arms profiled and articulated around the shaft in combination with the upper plate, the lower place being controlled by elastic components to be tensioned, when flexing the knee in combination with appropriate means, designed to suppress this control beyond a certain flexion angle, said means being fastened to a manual releasing component to fully suppress the elastic control.

Vallotton, U.S. Pat. No. 4,051,558 describes an artificial leg which includes a trunk socket, a thigh section hingably coupled to the trunk socket, a leg section hingably coupled to the thigh section and a foot section hingably coupled to the leg section. A mechanical energy storage device, such as a spring, is operatively associated with the artificial leg for storage and release of energy during a normal walking stride of the user. More particularly, energy is stored in the mechanical energy storage device during a weight-bearing phase of the walking stride when the user's weight is on the artificial leg and energy is released during a phase of the normal walking stride, when the user's weight is removed from the artificial leg. The stored energy is released from the energy storage device to pivot the thigh section forwardly about the hinged coupling thereof to the trunk socket. A dash-pot is coupled between the lower end of the thigh section and the foot section for damping flexion of the knee joint after a certain predetermined extent of ankle flexion is achieved to derive a more normal stride and cadence.

Asbelle, et al., U.S. Pat. No. 3,673,613 describes a variable friction knee unit that applies independent braking forces at different times to the swing phase of an artificial leg during walking which simulates the actions and efficiencies of the quadriceps and hamstring muscles of the thigh. Two braking modes are applied with an additional continuous braking mode. One operates at each end of swing phase. The second brake is applied a few degrees after the first brake and superimposed over the first brake. Both brakes are applied at each end of the swing phase of the walking cycle. In addition to being operative at the terminus of the swing, the two brakes are engaged at different times and are superimposed over the application of continuous friction so that the deceleration is a stepping function thereby simulating the function of the quadriceps and hamstring muscles of the thigh.

Adams, et al., U.S. Pat. No. 5,092,902 describes a prosthetic leg with a pivotal knee joint and a hydraulic fluid control unit connected to provide variable forces which dampen flexion and extension of the knee and also bias the leg to its extended position. The unit includes an aluminum housing lined with an axially adjustable sleeve and control bushing defining a cylindrical chamber which receives a piston mounted on a tubular position rod. The housing and chamber receive hydraulic fluid or oil which flows during movement of the piston through fluid control ports, channel and adjustable gaps defined by the sleeve and bushing for damping the movement of the rod. The piston rod encloses a gas filled flexible bladder which forms an oil accumulator during inward movement of the piston rod and also produces variable forces for moving the piston rod outwardly to its extended position. The housing confines a gap defining ring which compensates for changes in oil viscosity with heat.

Aulie, U.S. Pat. No. 5,171,325 describes a prosthetic joint which includes an anterior linking and support member and a posterior linking and support member, forming of a resilient material, which act as cantilever flat springs to provide an intrinsic extension bias while furnishing the rigid structure necessary to support the axial loads and extension movements induced by the amputee. A prosthetic knee joint includes a base formed of a resilient polyamide such as nylon 6/6, from which an anterior linking and support member, generally of an L-shape, and a posterior linking and support member, monolithically extend upwards. Formed to provide the inherent stability of four-bar linkage, these resilient linking and support members are pivotally attached to a yoke member to act as cantilever single-leaf flat springs which provide an intrinsic extension movement to the prosthetic knee joint which may vary according to the amount of flexion of the knee joint. The extension movement of the knee joint is translated into compression at the anterior linking and support member and tension at the posterior linking and support member, thereby allowing the use of a relatively low-strength resilient material in the knee joint construction. A common double-acting hydraulic damper is used to reduce the swing rate of the knee joint, permitting a desired gait and reducing terminal impact at full extension.

Glabiszewski, U.S. Pat. No. 4,595,179 describes a hydraulic damping unit, particularly for use in artificial joints. The unit includes a cylinder housing having a screw-in bottom part. A hollow piston is guided in the housing and has on its jacket a shoulder which delimits with corresponding flanges in the inner wall of the housing two chambers of variable volume for storing a hydraulic liquid. A hollow throttling piston is guided in the main piston and is formed with an annular recess which communicates with respective variable volume chambers via passages passing through the jacket of the main piston at both sides of the shoulder. In the range of both passages, the bottom of the recess of the throttling piston is connected to the outer surface of the latter via a sloping annular surface which, depending on the relative position of the throttling piston to the main piston, adjusts the clearance of the passages to control the resistance to flow of the hydraulic liquid. A set screw is arranged in the main piston opposite the end face of the throttling piston to adjust its axial position, and a counteracting return spring is arranged inside the throttling piston. Disclosed is also an artificial joint provided with the above hydraulic damping device. The lower part of the joint has a fork-shaped configuration, and the cylinder housing of the damping device is formed with pivot pins journalled in the opposite walls of the lower part. The main piston is linked to the upper part of the joint at a point which, in the aligned position of the upper and lower parts, is below the hinge axle of the joint.

Haupt, U.S. Pat. No. 4,685,927 describes a braked knee joint having a thigh part and a lower leg part which are provided with braking surfaces adapted to one another and which, because of the capacity for axial movement of the thigh part relative to the lower leg part, are pressed against one another during loading. The braking surfaces essentially have a contour which is circular in vertical section and which has a constant radius relative to the rotational axis. The joint includes a suitable stop to produce a jerk-free termination of the extension movement of the knee joint out of the flexed position. The stop is formed by providing the braking surface of the thigh part with a front end piece which is at a distance which increases from the rotational axis and is greater than the constant radius, and by providing a corresponding front end piece of the braking surface of the lower leg part so that, with increasing extension of the knee joint in the unloaded condition, a constantly increasing area of the braking surfaces comes into frictional contact and this forms the stop.

Nader, et al., U.S. Pat. No. 3,309,715 describes a safety knee for artificial legs with brake surfaces that can be more readily adjusted in order to compensate for wear and also for various specific tasks that the amputee may wish to perform. There will be a gradual wear of the brake linings and the present invention permits the knee to be adjusted for whatever wear may occur. There are certain tasks that necessitate a more abrupt adjustment. The invention has an aim for the adjustment of the braking surfaces through the user's clothing in order to either decrease or increase the clearances between the brake surfaces. In this regard, the brake surfaces can be adjusted so as to provide sufficient clearance in order to permit complete freedom of movement, such movement being desirable when riding a bicycles, for instance. If the amputee desires a completely rigid knee, such adjustment can also be achieved, thus permitting the user to walk on uneven ground, for instance. Consequently, the present invention provides a considerable amount of versatility as far as the adjustment feature is concerned.

Haupt, U.S. Pat. No. 4,685,926 describes an arrestable knee joint, comprising of a thigh member; a lower leg member; rotatably articulated on the thigh member to form a knee joint; and a mechanism for releasably arresting the members in the extended position, comprising a spring-loaded arresting element mounted in the lower leg member, structure associated with the thigh member for engaging the arresting element when the members are in the extend position, a rocker arm assembly having a first arm attached to the arresting element and a second arm extending away from a rotational axis of the rocker arm assembly on a side opposite from the first arm, and a Bowden wire inserted into the lower leg member and attached to the second arm of the rocker arm assembly. A release mechanism is provided in the thigh member.

Weber, et al., U.S. Pat. No. 4,135,254 describes a prosthetic knee apparatus which includes a pair of spaced side brackets depending from the upper leg prosthesis, and a housing disposed between the brackets. Extending through the housing to the brackets are anterior and posterior pivot shafts, the posterior pivot being provided with some play to permit a slight degree of pivot about the anterior shaft. A pair of leg brackets are also joined to the posterior pivot shaft with no play, and the housing is provided with a locking pin arrangement to releasably lock the leg brackets to the housing. The housing is provided with a pair of opposed braking pads which impinge on the leg brackets, the braking pads being actuated by a wedge which is driven into engagement by weight applied to the upper leg portion posteriorly of the anterior pivot shaft.

Wilkes, U.S. Pat. No. 4,005,496 describes a prosthetic knee joint having a femoral member and a tibial member each of which is provided with a bearing surface. The bearing surface of the tibial member supports the bearing surface associated with the femoral member such that flexion between the tibial member and the femoral member causes the respective bearing surfaces to roll relative to one another. Rollers, cam surfaces and guide slots are provided to ensure the retention of the proper relationship for this rolling contact between the tibial bearing surface and the femoral bearing surface. The knee joint includes a mechanical brake which produces a brake force that increased with flexure between the tibial member and the femoral member. The brake includes a resilient deformable element which transmits a brake applying force to a brake shoe which is operable along an axis generally perpendicular to the direction in which the force is applied. Hyperextension of the knee joint is mechanically limited and a torsion rod accommodates torsional motion between the knee joint and a lower leg to which it may be attached. The knee joint also includes a member which simulates the movement of the patella bone of a human knee.

NASA's Marshall Space Flight Center, Huntsville, Alabama has published a monograph describing a leg supporting device entitled Dual-Position Brace, and which is abstracted in *Popular Science*, May 1997, p27. This monograph describes a leg brace that lets the knee bend but locks in position when weight is put on the heel of the foot. This allows rehabilitation to begin before the knee can carry the full weight of the patient.

The prior art teaches the use of mechanical aids in providing support to the human knee joint, and replacement as well, and teaches several approaches to mechanically facilitating the functional use of a damaged knee joint for walking. However, the prior art does not teach a mechanical strut appliance capable of enabling a weak leg or a leg without knee function to perform a normal walking gait. The prior art does not teach a miniature and highly compact orthotic knee joint and brace having a pressure induced brake and a means for accelerating the rotation of the lower leg into a position for taking a load. The present invention fulfills these needs and provides further related advantages as described in the following summary.

SUMMARY OF THE INVENTION

As an introduction to the present invention it is desirable to understand the basic physics of the human stride or gait. This is well presented in a chapter entitled; "Kinesiology of Functional Characteristics of the Lower Limb," see pages 264–267, in the *Atlas of Limb Prosthetics*, written by The American Academy of Orthopaedic Surgeons, and published by C. V. Moshy, 1981, and which is incorporated into this application by reference and made a part thereof.

The present invention teaches certain benefits in construction and use which give rise to the objectives described below. The invention assists or takes the place of muscles which are either weak or absent and which normally control and prevent the knee from buckling at heel strike through terminal stance, and which also help to move the knee to move from a flexed attitude during the swing phase up to the straight leg position just before initial contact with the floor. The engineering principles embodied by the present invention may be used in an orthotic embodiment as is described and shown here, or may be alternately used in a prosthetic embodiment as will be easily completed by those of skill in the art from a knowledge of the present presentation.

The present invention provides a weight bearing strut assembly capable of supporting the human frame in the act of walking, of enabling a leg to which it is attached to bend in a normal manner as the leg is brought forward during each step, and to lock when the leg is straightened as necessary in preparation of shifting weight thereupon. The strut assembly includes an upper and lower portions proving a braking mechanism activated as load is placed upon the strut assembly, and a motion urging mechanism activated when the load is removed, and the lower portion of the strut assembly is rotating toward forming a straight-leg attitude. Under these conditions, the motion urging mechanism drives the strut assembly quickly into a co-linear arrangement so as to assure that the strut assembly is ready to take a compressive load prior to weight transfer.

A primary objective of the present invention is to provide an orthopaedic appliance capable of providing support to the human frame during the act of walking, i.e., enabling a leg to which it is attached to move through the normal and natural human ambulatory motions in a manner not taught by the prior art.

Another objective is to provide such an appliance having a stationary upper linear member rotationally joined with a lower linear member, the members being attached to the upper and lower leg portions of the human leg respectively.

A further objective of the invention is to provide such an appliance having a braking capability so as to prevent relative rotation between the upper and lower members when weight is applied to the appliance thereby preventing buckling forward of the invention when weighted.

A still further objective of the invention is to provide such an appliance with a motion accelerating or urging capability such that the lower member is quickly rotated into co-linearity with the upper member when the forward moving leg needs to straighten-out in preparation for receiving weight.

A further objective is to provide such an appliance whereby the urging force is adjustable and whereby the relationship between force and the angular position of the lower member is adaptable for individual needs.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 1 is a front elevational view of the preferred embodiment of the present invention;

FIG. 2 is a side elevational view thereof,

FIG. 4 is a rear elevational view thereof with an upper and lower struts of the invention co-linearly aligned;

FIG. 5 is a rear elevational view similar to FIG. 4 when the upper and lower struts of the invention are positioned at a relatively slight angle of departure from the straight angle;

FIG. 6 is a rear elevational view similar to FIG. 4 when the upper and lower struts of the invention are positioned at a relatively large angle of departure from the straight angle;

FIG. 7 is a front elevational view showing internal details of a braking means thereof when the braking means is not applied;

FIG. 8 is a close-up view of a roller bearing shown in FIG. 7;

FIG. 9 is a front elevational view showing internal details of the braking means thereof when the braking means is applied; and FIG. 10 is a close-up view of the roller bearing shown in FIG. 9.

DETAILED DESCRIPTION OF THE INVENTION

Figure 3:
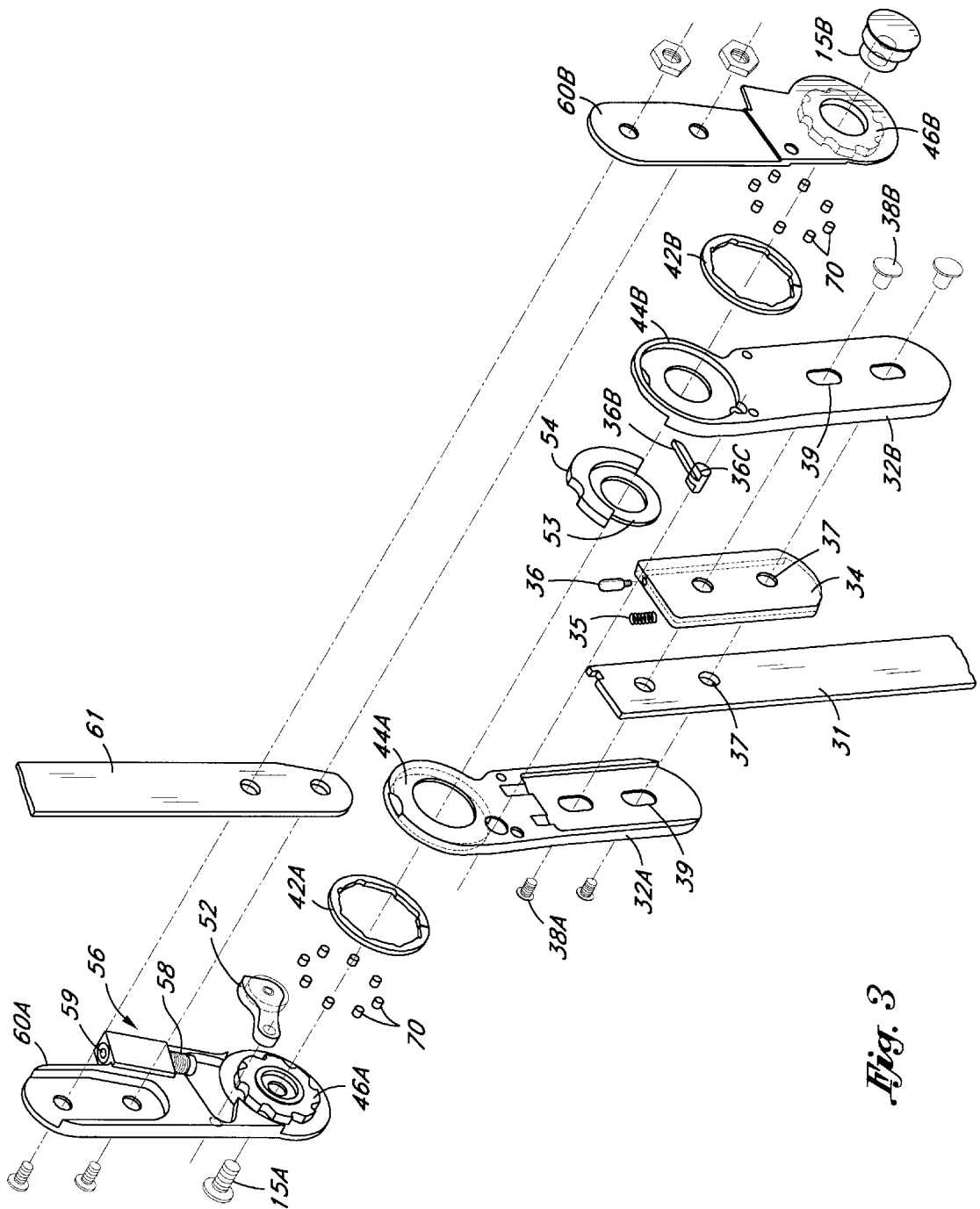
FIG. 3 is an exploded perspective view thereof showing the individual parts and their mutual relationship.

The above described drawing figures illustrate the preferred embodiment of the present invention, an orthopaedic appliance 10 for facilitating walking when the human leg or knee is damaged or inoperable. FIGS. 1 and 2 show the invention as it is applied to the human leg and provide an understanding of the overall appearance and structure of the invention. The appliance 10 comprises an upper strut assembly 20 hingably engaged with a lower strut assembly 30 by a hinge means 15 comprising screw 15A and nut 15B, and includes a means for braking 40 and a means for urging motion 50. The lower strut assembly 30 is rotatable from a first position 30A, as shown in FIG. 4, forming a straight angle with the upper strut assembly 20, to a second position 30B shown in FIG. 6, forming an acute angle α, typically in the range of at least 75 degrees, therewith, the lower strut assembly 30 further being adapted for linear translation toward and away from the upper strut 20, as shown in FIGS. 7 and 9.

Referring now to FIG. 3 we see that the means for braking 40 is adapted for providing strong resistance to relative rotation between the strut assemblies 20 and 30 when the lower strut assembly 30 is driven toward the upper strut assembly 20 as when the terminal end 32 (FIG. 1) is pressed into contact with a walking surface such as a street or building floor surface, etc., and the body weight of the individual is transferred to the leg to which the appliance 10 is attached. The motion braking means 40 provides a split brake band means 42, comprised of a brake band A, 42A and a brake band B, 42B, which are engaged within a brake drum means 44 comprising brake drum A, 44A and brake drum B, 44B respectively. The lower strut assembly 30 performs a linear translation within a lower hinge case means 32 comprising lower hinge case A, 32A and lower hinge case B, 32B. This linear motion toward the upper strut assembly 20 expands the split brake band means 42 radially within the brake drum means 44 causing frictional engagement therebetween so as to thwart relative motion between the strut assemblies 20 and 30. This occurs because the brake drum means 44 is normally able to freely rotate about brake hub means 46 comprising brake hub A, 46A and brake hub B, 46B and is also normally able to rotate freely about brake band means 42. Lower strut assembly 30 comprises a lower strut 31, a brake actuating slipper 34, return spring 35, braking finger 36A and retaining screws 38A and retaining nuts 38B, fasteners which join the foregoing parts with lower hinge case means 32 through round holes 37 and elongated holes 39 as shown in FIG. 3 such that the lower strut assembly 30 is able to slide in translation within lower hinge case means 32. Notice that the elongated holes 39 enable fasteners 38A and 38B to move therein. When weight is placed upon the lower strut 31 the lower strut assembly 30 moves in linear translation, causing braking finger 36 to press against and rotate braking arm 36B. Braking element 36C is then rotated into contact with brake band means 42 causing it to start to rotate along with lower hinge case means 32. Just as soon as brake band means 42 starts to rotate relative to brake hub means 46, the plurality of roller bearings 70 are forced to move in the direction of motion of brake band means 42 and start to roll upward on inclined surfaces 72 (FIG. 10). This causes the roller bearings 70 to move radially outward against brake band means 42, which, in turn, causes brake band means 42 to engage brake drum means 44. The net result is that the braking force is amplified so as to strongly prevent rotation of lower strut assembly 30 relative to upper strut assembly 20. As shown in FIG. 7, when weight is removed from the appliance, the return spring 35 causes the brake actuating slipper 34 to move downwardly releasing the braking arm 36.

Notice that the brake band means 42 is circular in shape and is radially split so as to enable radial outward expansion thereof. Notice too, that the plurality of roller bearings 70 are positioned for rolling within roller slots 71 between the brake band means 42 and the brake hub means 46, the roller slots 71 being shaped to cause the roller bearings 70 to force the brake band means 42 radially outwardly and into contact with the brake drum means 44.

The means for urging motion 50 is adapted for rotating the lower strut assembly 30 toward the straight angle position 30A when the lower strut assembly 30 moves within a specified angle, preferably approximately α=162 degrees, i.e., near the straight angle. This action is best shown and is clearly understood by observing FIGS. 4, 5, and 6. As shown, the urging motion means 50 preferably provides a cam follower 52 in rolling engagement with a camming surface means 53, a washer-like device, having a camming surface 54 such that the cam follower 52 rolls on the camming surface 54 whenever the relative angle 60 between the strut assemblies 20, 30 is changing. The cam follower 52 is forced into contact with the camming surface 54 by a cam loading means 56, the camming surface 54 providing a camming groove 54A such that with the strut assemblies 20, 30 in near straight angle alignment, i.e., in the neighborhood of approximately α=162 angular degrees, as shown in FIG. 5, the cam follower 52 enters the camming groove 54A and thereby urges the lower strut assembly 30 to move into the straight angle relationship with upper strut assembly 20 as shown in FIG. 4. It is clearly seen in FIG. 6. that the cam loading springs 58 press the cam follower 52 radially against the camming surface means 53 thereby developing no tangentially directed component of force against the camming surface means 53 and therefore does not urge the rotation of the camming surface means 53. It is also seen, primarily in FIG. 4, that when the cam follower 52 enters the camming groove 54A, a tangential component of the force is developed, thereby causing the camming surface means 53 to rotate under a high force directed by the cam follower 52. Thus the rotating force on the camming surface means 53 corresponds directly to the contour of the camming surface means 53. The curvature of the camming surface 54 as well as the camming groove 54A and the curvature of their transition is preferably customized to fit the needs of each individual in accordance with their particular walking gait, length of leg, ratio of upper to lower leg proportion and other physical characteristics that determine gait and especially the moment when the lower leg should quickly recover its co-linear relationship. The camming surface means 53 is preferably constructed as a replaceable washer-shaped element as shown in FIG. 3 so as to be easily removed from the invention for modification and adaptation to the needs of a particular individual. Thus, a proper leg swing and lower leg return timing and motion characteristic can be matched to the individual's needs. The cam loading means 56 preferably includes cam loading springs 58, preferably a stack of bellville (wave) washers which can exert a very high force over a short flexture distance, and a spring tensioning screw 59 capable of being tightened down onto the springs 58. Notice that cam follower 52 rotates about pin 52A under the considerable force of springs 58. They are capable of exerting enough force to cause lower strut assembly 30 to move rapidly toward co-linearity with upper strut assembly 20 at the appropriate point in the swinging motion experienced by the strut assembly 90. It should be noted that upper hinge case means 60 comprises upper hinge case A, 60A and upper hinge case B, 60B, which join upper strut 61 in a sandwich assembly held by fasteners as shown in FIG. 3.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An orthopaedic appliance comprising:
   an upper strut assembly hingably engaged with a lower strut assembly by a hinge means for rotational motion of the lower strut assembly from a first position, forming an approximate straight angle with the upper strut assembly, to a second position, forming an acute angle therewith, the lower strut assembly further being adapted for linear translation toward and away from the hinge means;
   a means for braking engaged with the hinge means and adapted for providing resistance to the rotating of the lower strut assembly when the lower strut assembly translates toward the hinge means;
   a means for urging motion engaged with the hinge means and adapted for providing an urging force directed for urging the lower strut assembly toward the first position, the magnitude of the urging force corresponding to a camming surface contour of a camming surface means of the means for urging motion.

2. The appliance of claim 1 further including a cam follower positioned for moving on the camming surface and a cam loading means urging the cam follower thereagainst, wherein at least a portion of the camming surface contour is adapted to preferentially rotate the lower strut assembly toward the first position.

3. The appliance of claim 1 wherein the camming surface contour provides a camming groove as a rest position for the cam follower such that with the cam follower engaged within the camming groove, the lower strut tends to remain in the first position.

4. The appliance of claim 2 wherein the cam loading means is a stack of wave washers, the washers being tensioned by a spring tensioning screw.

5. The appliance of claim 1 wherein the lower strut assembly includes a brake drum means, the braking means providing a brake band means concentrically positioned and rotatable within the brake drum means, the brake band means expandable radially outwardly to engage the brake drum means for retarding rotation of the lower strut assembly.

6. The appliance of claim 5 wherein the upper strut assembly includes a brake hub means positioned concentrically within the brake band means and wherein a plurality of roller bearings are positioned for rolling within roller slots between the brake band means and the brake hub means, the roller slots being shaped to cause the roller bearings to force the brake band means radially outwardly when the brake band means is prevented from rotating with the brake hub means.

7. The appliance of claim 6 further including a rotational brake element positioned for actuation by linear translation of the lower strut assembly, said brake element applying a braking force to the brake band means to halt rotation of the brake band means with the brake hub means thereby driving the roller bearings against the brake band means for expansion against the brake drum means for resisting rotation of the lower strut assembly.

* * * * *